(12) United States Patent
Mueller et al.

(10) Patent No.: US 7,524,500 B2
(45) Date of Patent: Apr. 28, 2009

(54) METHOD OF STIMULATING STEM CELLS

(75) Inventors: Susan Mueller, Milton (CA); David Bell, Oakville (CA); Kathryn Emma Matthews, Toronto (CA)

(73) Assignee: Therapure Biopharma Inc., Mississauga, Ontario (CA)

( * ) Notice: Subject to any disclaimer, the term of this patent is extended or adjusted under 35 U.S.C. 154(b) by 72 days.

(21) Appl. No.: 10/471,604

(22) PCT Filed: Mar. 26, 2002

(86) PCT No.: PCT/CA02/00411

§ 371 (c)(1),
(2), (4) Date: Mar. 26, 2004

(87) PCT Pub. No.: WO02/076501

PCT Pub. Date: Oct. 3, 2002

(65) Prior Publication Data

US 2004/0151692 A1    Aug. 5, 2004

Related U.S. Application Data

(60) Provisional application No. 60/341,793, filed on Dec. 21, 2001, provisional application No. 60/278,453, filed on Mar. 26, 2001.

(51) Int. Cl.
*A61K 39/40* (2006.01)
*A61K 35/26* (2006.01)

(52) U.S. Cl. .................. 424/139.1; 424/577
(58) Field of Classification Search .......... None
See application file for complete search history.

(56) References Cited

FOREIGN PATENT DOCUMENTS

WO    WO 02/32941 A2    4/2002

OTHER PUBLICATIONS

Feldman et al., Transplant. Proc. 1998, 30, 4126-4127.*
Cochlovius et al., Modern Drug Discovery, 2003, pp. 33, 34, 37, 38.*
Matthews et al., Stem Cells and Development, 2006, vol. 15, pp. 40-48.*
Bachil et al., J of Leukocyte Biology, 2006, vol. 79, pp. 312-318.*
Stec et al., J of Leukocyte Biology, 2007, V. 82, pp. 594-602).*
Sanchez, C. et al., *The procin 2A10 antigen is homologous to human CD163 and related to macrophage differentiation*, Journal of Immunology, May 1, 1999, 162(9): 5230-5237.
Kristiansen, Mette et al., *Identification of the haemoglobin scavenger receptor*, Nature, 409(6817):198-201.

* cited by examiner

*Primary Examiner*—Michail A Belyavskyi
(74) *Attorney, Agent, or Firm*—Bereskin & Parr; Micheline Gravelle

(57) ABSTRACT

Methods and compositions for stimulating the growth, proliferation, differentiation and/or mobilization of stem and/or progenitor cells are described. The method involves administering an effective amount of a substance which can activate the CD163 hemoglobin scavenger receptor signal transduction pathway. The methods and compositions are useful in stimulating hematopoiesis and in treating a wide range of conditions including cytopenias, anemias and for use in preparing cells for transplantation.

6 Claims, 3 Drawing Sheets

METHOD OF STIMULATING STEM CELLS

FIELD OF THE INVENTION

The present invention relates to methods and compositions for stimulating the growth, proliferation, differentiation and/or mobilization of stem cells leading to the production of blood cells. More specifically, this invention relates to a method of stimulating hematopoiesis, including stimulating erythropoiesis and myelopoiesis, through the stimulation of stem cells, and erythroid and myeloid progenitor cells, respectively.

BACKGROUND OF THE INVENTION

A hemoglobin scavenger receptor has recently been identified on monocytes and macrophages (Kristiansen, 2001). This receptor scavenges hemoglobin by mediating endocytosis of haptoglobin-hemoglobin complexes. This receptor has also been identified as M130/CD163, an acute phase-regulated transmembrane protein that has been reported to be expressed exclusively on monocytes and macrophages. CD163 belongs to the group B scavenger receptor cysteine-rich superfamily, a family of receptors that includes CD5, CD6 and WC1 which are present on B, T and $CD4^-8^-\gamma\delta$ T lymphocytes, respectively. Complexes of hemoglobin and multimeric haptoglobin exhibit higher functional affinity for CD163 than do complexes of hemoglobin and dimeric haptoglobin.

Previous studies of antibody-mediated crosslinking of CD163 on cultured monocytes have demonstrated that ligation of surface CD163 induces tyrosine kinase—dependent signals resulting in the mobilization of intracellular calcium, inositol triphosphate production and increased secretion of anti-inflammatory cytokines, including interleukin 6 (IL-6) and granulocyte-macrophage colony stimulating factor (GM-CSF) (van den Heuvel et al, 1999).

Hematopoiesis is defined as the production and development of blood cells, including erythrocytes, granulocytes, monocytes, macrophages, esoinophils, basophils, megakaryocytes, B cells and T cells (Wintrobe, 1999). Hematopoiesis occurs as the result of the proliferation and differentiation of hematopoietic stem cells. Hematopoietic stem cells are pluripotent cells which can give rise to the multiple cell lineages found in the blood. Hematopoietic stem cells reside in the bone marrow and their growth, proliferation and differentiation are influenced by both hematopoietic growth factors and the stromal cells within the bone marrow. Stem cells are believed to normally reside in a quiescent nondividing state until stimulated by specific growth factors whereupon they divide and give rise to highly proliferative progenitor cells committed to the production of blood cells of one or more lineages, such as the erythroid, myeloid or lymphoid lineages.

Certain clinical disorders, termed cytopenias, are characterized by the decreased level of a specific cell type in the circulating blood. For example neutropenia is a disorder whereby there is a diminished level of circulating neutrophils. This disorder can be treated by GM-CSF or G-CSF, two different hematopoietic growth factors. However, administration of these growth factors is often associated with a high incidence of adverse side effects. For example, the administration of G-CSF after allogeneic bone marrow transplantation may result in dyspnea, chest pain, nausea, hypoxemia, diaphoresis, anaphylaxis, syncope and flushing (Khoury et al, 2000).

Neutropenia is also associated with AIDS and is currently treated with growth factors (Dubreuil-Lemaire et al, 2000). There are also forms of severe congenital neutropenia (Dale et al, 2000) in which a small percentage of the patients are refractory to the administration of growth factors.

Anemia is the pathological consequence of insufficient hemoglobin to meet the oxygen transport requirements of the body. Historically, certain anemias have been treated with blood or red blood cell transfusions. A variety of complications associated with transfusions makes this treatment undesirable, including hemolytic, febrile and allergic reactions, along with the potential of the transmission of disease. Stimulating the growth and development of erythroid cells (erythropoiesis) is desirable in the treatment of anemia. There are several causes of anemia, which include excessive blood loss, increased red blood cell destruction, decreased synthesis of red blood cells and abnormal production of hemoglobin. Decreased red blood cell production may result from an iron deficiency (either dietary, maladsorption from the gastrointestinal tract, ineffective iron transport or iron utilization by developing red cells), insufficient erythropoietin (Epo) production (kidney dysfunction) or bone marrow failure. Since the erythropoietic activity of the bone marrow is intact in iron and Epo-dependent anemias, such anemias are amenable to iron or Epo therapy, respectively.

Anemia due to iron-deficiencies is typically treated by the oral or intravenous administration of iron. Patients with chronic renal failure typically suffer from Epo-dependent anemias due to the inability of the kidneys to produce Epo. These patients undergo dialysis and 90% are clinically anemic. The traditional treatment for anemia in dialysis patients consisting of multiple blood transfusions has largely been replaced by the administration of Epo. Indeed, ~88% of all dialysis patients are treated with Epo. One third of patients on Epo therapy develop hypertension, which can generally be corrected using anti-hypertensive drugs. Erythroid progenitors are stimulated by Epo to differentiate into mature red blood cells and synthesize hemoglobin, the main red blood cell protein.

A major limiting factor of Epo therapy is the cost of long term treatment. Typical Epo doses for patients with chronic renal failure are 225 Units/kg/week administered in three doses. Medicare reimbursement for Epo treatment in the U.S. is $10.00 per 1,000 Units, thus the typical cost for a 70 kg patient would be ~$8,000 yearly. In 1995, 175,000 US patients were on dialysis resulting in a market in excess of $883 million for this indication alone. Costs for this therapy are estimated to be ~$1.1 billion for 1996. Novel therapies which would reduce Epo requirements for the treatment of anemia would thus be beneficial to the patient and to the healthcare system. The discovery of other agents capable of reducing Epo requirements for the treatment of Epo-dependent anemias would be advantageous.

Furthermore, there are a variety of anemias which do not respond to Epo therapy. Examples of these types of anemia include chemotherapy-induced anemia and anemia of chronic disease, including malignancies. Patients with acquired immunodeficiency can also suffer from anemia, as do AIDS patients being treated with AZT. These types of anemia may be due to ineffective erythropoiesis as a result of either suppressed Epo production or a decreased response of the bone marrow to Epo. Treatment of these types of anemia involves treatment of the primary disorder; however, if the primary disorder cannot be readily treated, then the therapy for the anemia can include red blood cell transfusions.

Adverse side-effects of transfusions include acute and delayed hemolytic reactions and the potential of transfusion of transmittable diseases.

In view of the foregoing, there is a need in the art to develop improved methods for increasing the number of blood cells in a patient through the stimulation of hematopoiesis.

SUMMARY OF THE INVENTION

The present inventors have determined that activation of the hemoglobin scavenger receptor, CD163, can stimulate the growth, proliferation and differentiation of both erythroid and myeloid progenitors, leading to increased blood cell production. The inventors have also demonstrated that CD163 is expressed by $CD34^+$ hematopoietic stem cells.

Accordingly, the present invention provides a method of stimulating the growth, proliferation, differentiation and/or mobilization of a stem cell capable of expressing the CD163 receptor, or responding to the signal transduction pathway stimulated by the receptor, comprising administering an effective amount of a substance that can activate CD163 on the stem cell, to a cell or an animal in need thereof.

The present invention also provides a method of stimulating hematopoiesis comprising administering an effective amount of a substance that can activate CD163 to a cell or an animal in need thereof.

The present invention further provides a method of stimulating erythropoiesis comprising administering an effective amount of a substance that can activate CD163 to a cell or an animal in need thereof.

The present invention yet also provides a method of stimulating myelopoiesis comprising administering an effective amount of a substance that can activate CD163 to a cell or an animal in need thereof.

The present invention also includes pharmaceutical compositions comprising an effective amount of a substance that can activate CD163 in admixture with a suitable diluent or carrier.

The present invention further provides a cell culture additive useful for enhancing growth, proliferation, differentiation and/or mobilization of stem and/or progenitor and cells comprising an effective amount of a substance that can activate CD163.

The present invention also provides a method of selecting stem or progenitor cells in a sample comprising (a) contacting the sample with a substance that can bind CD163 and (b) selecting cells that are bound to the substance.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art of this detailed description.

BRIEF DESCRIPTION OF THE DRAWINGS

The invention will now be described in relation to the drawings in which.

DETAILED DESCRIPTION OF THE INVENTION

I. Methods of the Invention

Figure 1:
FIG. 1 is a Western blot analysis of $CD34^+$ cells using an anti-CD163 antibody.

As hereinbefore mentioned, the present inventors have demonstrated that $CD34^+$ stem cells express the hemoglobin scavenger receptor, CD163. Accordingly, the present invention provides a method of stimulating the growth, proliferation, differentiation and/or mobilization of a stem cell comprising administering an effective amount of a substance that can activate CD163 on the stem cell to a cell or an animal in need thereof. The present invention also provides a use of an effective amount of a substance that can activate CD163 to stimulate the growth, proliferation, differentiation and/or mobilization of a stem cell. The present invention further provides a use of an effective amount of a substance that can activate CD163 to prepare a medicament to stimulate the growth, proliferation, differentiation and/or mobilization of a stem cell.

The phrase "substance that can activate CD163" as used herein includes all substances that can bind, crosslink or ligate the CD163 hemoglobin scavenger receptor or a CD163 related receptor on cells and result in the stimulation of growth, proliferation, differentiation and/or mobilization of the cell. The term also includes any substance that can activate a signal transduction pathway that is activated in response to activation of CD163 or a CD163-related receptor. For example, the substance may activate the downstream signal transduction pathways that are activated in response to activation of CD163, including but not limited to tyrosine kinases, calcium mobilization and inositol triphosphate (IP3) and inositol tetrakisphosphate (IP4) mobilization. The phrase "substance that can activate CD163 pathway" further includes any substance that blocks the inactivation of any signal transduction pathways that are activated in response to activation of CD163 or a CD163-related receptor.

The phrase "stimulate the growth, proliferation, differentiation and/or mobilization of a stem cell" as used herein means that the substance can stimulate or enhance the growth, proliferation, differentiation and/or mobilization of a stem cell as compared to the growth, proliferation, differentiation and/or mobilization of a stem cell in the absence of the substance.

The term "effective amount" as used herein means an amount effective and at dosages and for periods of time necessary to achieve the desired result (e.g., the stimulation of the growth, proliferation, differentiation and/or mobilization of stem cells, erythroid and/or myeloid progenitor cells and/or the stimulation of hematopoiesis, erythropoiesis or myelopoiesis).

The term "animal" as used herein includes all members of the animal kingdom and is preferably human. Administering a substance to an animal includes both in vivo and ex vivo administrations.

The term "a cell" as used herein includes a single cell as well as a plurality or population of cells. Administering a substance to a cell includes both in vitro and in vivo administrations.

The term "stem cell" as used herein means a cell that is capable of differentiating into any cell including hematopoietic cells in an animal. The stem cell will express or will be capable of expressing the CD163 receptor or responding to the signal transduction pathway stimulated by the receptor.

Preferably, the stem cell is a $CD34^+$ stem cell. $CD34^+$ cells are traditionally considered "stem" cells in that they are capable of both self-renewal and re-populating an individual with cells from all hematopoietic lineages. $CD34^+$ cells are further delineated into sub-populations by the co-expression of other markers, such as CD38, and the ability of these sub-populations to re-engraft and repopulate the hematopoietic system (eg., Henon et al., 2001).

Stimulating stem cells may facilitate the mobilization of stem cells from extravascular marrow sites to circulating blood which is required for protocols using donor peripheral blood for autologous or heterologous transplantation. Recombinant human G-CSF is widely used for mobilizing $CD34^+$ stem cells (for review, see Korbling, 1998). As the inventors have demonstrated the expression of CD163 by $CD34^+$ cells, it may be possible that stimulation of the CD163 pathway on said cells will result in their growth and proliferation and possible mobilization to the peripheral blood. Use of CD163 stimulators (for example, a cross-linking antibody) instead of, or in conjunction with reduced amounts of, G-CSF may result in the mobilization of transplantable stem cells without the side effects that may be associated with cytokine administration.

The inventors have shown that activating the CD163 pathway may be useful in stimulating multi-lineage hematopoiesis as they have shown that both erythroid and myeloid progenitor cells can be stimulated by activating CD163. Stimulating hematopoiesis is useful in generating both blood cells and cells of the immune system including erythrocytes, myeloid cells (such as monocytes, macrophages, eosinophils, neutrophils, basophils and megakaryocytes) and lymphoid cells (B cells, T cells and NK cells), as well as dendritic cells of both myeloid and lymphoid origin.

Accordingly, the present invention provides a method of stimulating hematopoiesis comprising administering an effective amount of a substance that can activate CD163 to a cell or an animal in need thereof. The present invention also provides a use of an effective amount of a substance that can activate CD163 to stimulate hematopoiesis. The present invention further provides a use of an effective amount of a substance that can activate CD163 to prepare a medicament to stimulate hematopoiesis.

Stimulating hematopoiesis is useful in treating a wide range of conditions, including cytopenias as well as in stimulating the development of blood cells for use in transplantation or stimulating cells of the immune system for use in treating immune deficiencies.

The phrase "stimulate hematopoiesis" as used herein means that the substance can stimulate or enhance the growth, proliferation, differentiation and/or mobilization of a hematopoietic stem cell or a hematopoietic progenitor cell (such as an erythroid, myeloid or lymphoid progenitor) as compared to the growth, proliferation, differentiation and/or mobilization of a hematopoietic stem cell or progenitor cell in the absence of the substance.

One skilled in the art can determine whether or not the substance that can activate CD163 can stimulate hematopoiesis. For example, the colony forming assay is a method to quantify hematopoietic stem cells and progenitors (McCulloch, 1984). In the colony forming assay, cells are plated into a semi-solid medium such as methylcellulose in the presence of various cytokines which support hematopoietic progenitor cell growth, survival and differentiation. The types of hematopoietic colonies which form include: burst forming unit—erythroid (BFU-E), colony forming unit—erythroid (CFU-E), colony forming unit—granulocyte macrophage (CFU-GM), colony forming unit—macrophage (CFU-M), colony forming units—megakaryocyte (CFU-Meg) and granulocyte, erythroid, monocyte and megakaryocyte (GEMM) colonies. In semi-solid assays, stem or progenitor cells respond to a variety of cytokines and various combinations of these cytokines have been optimized for the growth and differentiation of erythroid progenitors (for example, IL-3 in combination with EPO) or granulopoeitic/monocyte colonies (for example, IL-1β, IL-6 and SCF). Some combinations are required to enumerate both myeloid and erythroid colonies independently, in addition to the enumeration of more primitive "mixed" colonies (for example, those that include either G-CSF and GM-CSF, for review see Messner; 1991, 7:18-22). Each stem cell or progenitor cell proliferates and differentiates to form a morphologically distinct colony. The two kinds of functionally distinct erythroid progenitors (BFU-E and CFU-E) are identified based on their abilities to form morphologically recognizable colonies when grown in semi-solid media. The BFU-E represents the most primitive erythroid progenitor and forms large multi-clustered, hemoglobinized colonies. The CFU-E is a more differentiated erythroid progenitor which forms smaller, hemoglobinized colonies. The BFU-E is the earliest identifiable progenitor fully committed to erythropoiesis and has a larger capacity for self-renewal that the more mature CFU-E. To develop, erythroid progenitor colonies typically require the presence of erythropoietin (Epo) in the media. Early on however, primitive erythroid progenitors proliferate in an Epo-independent fashion.

Along with providing a means to quantify hematopoietic stem cells and progenitors, the colony forming assay also provides a means to obtain information about factors affecting the proliferation and differentiation of the progeny of the stem and progenitor cells. For example, erythroid progenitor colonies arise from a single progenitor cell which divides and differentiates such that the mature colony is composed predominantly of hemoglobinized erythroblasts. Morphologically, the size of an erythroid colony may provide information on the rate or extent of proliferation of the progeny of the erythroid progenitor. Also, a redder erythroid colony would suggest a greater hemoglobin content, and possibly a greater degree of differentiation of the erythroblasts.

As mentioned previously, the inventors have shown that activation of CD163 increases the proliferation and differentiation of erythroid cells. Accordingly, in another embodiment, the present invention provides a method of stimulating erythropoiesis comprising administering an effective amount of a substance that can activate CD163 to a cell or an animal in need thereof. The present invention also provides a use of an effective amount of a substance that can activate CD163 to stimulate erythropoiesis. The present invention further provides a use of an effective amount of a substance that can activate CD163 to prepare a medicament to stimulate erythropoiesis.

The phrase "stimulate erythropoiesis" as used herein means that the substance can stimulate or enhance the growth, proliferation, differentiation and/or mobilization of an erythroid cell or an erythroid progenitor cell or a stem cell as compared to the growth, proliferation, differentiation and/or mobilization of an erythroid cell or an erythroid progenitor or a stem cell in the absence of the substance. One skilled in the art can determine whether or not the substance that can activate CD163 can stimulate erythropoiesis. For example, the colony forming assay described above and in the Examples can be used.

Stimulating erythropoiesis is useful in treating anemia. Accordingly, in a specific embodiment, the present invention relates to a method of treating anemia comprising administering an effective amount of a substance that can activate CD163 to a cell or animal in need thereof. The present invention also provides a use of an effective amount of a substance that can activate CD163 to treat anemia. The present invention further provides a use of an effective amount of a substance that can activate CD163 to prepare a medicament to treat anemia.

The inventors have also shown that activating CD163 increases the proliferation of myeloid cells. Accordingly, in another embodiment, the present invention provides a method of stimulating myelopoiesis comprising administering an effective amount of a substance that can activate CD163 to a cell or animal in need thereof. The present invention also provides a use of an effective amount of a substance that can activate CD163 to stimulate myelopoiesis. The present invention further provides a use of an effective amount of a substance that can activate CD163 to prepare a medicament to stimulate myelopoiesis.

The phrase "stimulate myelopoiesis" as used herein means that the substance can stimulate or enhance the growth, proliferation, differentiation and/or mobilization of a myeloid cell or a myeloid progenitor cell or a stem cell as compared to the growth, proliferation, differentiation and/or mobilization of a myeloid cell or a myeloid progenitor cell or a stem cell in the absence of the substance. One skilled in the art can determine whether or not the substance that can activate CD163 can stimulate myeloid cells. For example, the colony forming assay described above and in the Examples can be used.

Stimulating the growth, proliferation, differentiation and/or mobilization of myeloid cells can be used to treat neutropenias. Stimulation of myeloid cells through CD163 activation of the CD163 pathway may replace/augment the effectiveness of growth factors in overcoming neutropenias associated with bone marrow transplants with the added benefit of fewer side effects. The method can additionally be used to treat neutropenias associated with AIDS or severe congenital neutropenias. Accordingly, in a specific embodiment, the present invention provides a method of treating a neutropenia comprising administering an effective amount of a substance that can activate CD163 to a cell or animal in need thereof. The present invention also provides a use of an effective amount of a substance that can activate CD163 to treat a neutropenia. The present invention further provides a use of an effective amount of a substance that can activate CD163 to prepare a medicament to treat a neutropenia.

As used herein, and as well understood in the art, "to treat" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

II. Substances that Activate CD163

The present invention includes the use of any and all substances that can activate CD163 (as defined above) in the methods of the invention. The substance can be any type of substance, including but not limited to, proteins (such as antibodies), peptides, nucleic acids, carbohydrates, organic compounds, inorganic compounds, small molecules, drugs, CD163 ligands, soluble forms of the CD163 receptor, any and all CD163 agonists as well as any and all substances that inhibit CD163 antagonists.

In a preferred embodiment, the substance that activates CD163 is a substance that binds the CD163 receptor on the cell being treated. Examples of substances that bind CD163 include antibodies and CD163 ligands.

(a) Antibodies

In a specific embodiment, the substance that can activate CD163 is an antibody that binds to the CD163 receptor. Antibodies to CD163 can be from readily available commercial sources for example from Serotec Inc. or Maine Biotechnology Services. Further, one skilled in the art can readily prepare antibodies to CD163 using techniques known in the art such as those described by Kohler and Milstein, Nature 1975, 256: 495 and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

For example, by using a peptide of CD163, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated.

The term "antibody" as used herein is intended to include fragments thereof which also specifically react with CD163, or a peptide thereof. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes CD163 antigens. (See, for example, Morrison et al., Proc. Natl. Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B). It is expected that chimeric antibodies would be less immunogenic in a human subject than the corresponding non-chimeric antibody.

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against CD163 may also be generated by screening expression libraries encoding immunoglobulin genes, or portions thereof, expressed in bacteria with peptides produced from the nucleic acid molecules encoding CD163 or parts thereof. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al., Nature 348, 552-554 (1990)). Alternatively, a SCID-hu mouse, for example the model developed by Genpharm Inc, can be used to produce antibodies or fragments thereof.

The antibodies of the invention also include bifunctional antibodies comprising an antibody specific for CD163 linked directly to another antibody specific for another antigen on the surface of the stem cell. Bifunctional antibodies may be prepared by chemically coupling one antibody to the other, for example by using N-succinimidyl-3-(2-pyridyldithio) propionate (SPDP). The antibodies of the invention also include bispecific antibodies. Bispecific antibodies contain a variable region of an antibody specific for CD163 and a variable region specific for at least one antigen on the surface of the stem cells to be targeted. The bispecific antibodies may be prepared by forming hybrid hybridomas. The hybrid hybridomas may be prepared using the procedures known in the art such as those disclosed in Staerz & Bevan, (1986, PNAS (USA) 83: 1453) and Staerz & Bevan, (1986, Immunology Today, 7:241). Bispecific antibodies may also be constructed by chemical means using procedures such as those described by Staerz et al., (1985, Nature, 314:628) and Perez et al., (1985 Nature 316:354), or by expression of recombinant immunoglobulin gene constructs.

(b) Other Substances

In addition to antibodies, other substances that can activate CD163 can also be identified and used in the methods of the invention. For example, substances which can bind CD163 on stem cells or progenitor cells may be identified by reacting CD163 with a substance which potentially binds to CD163, then detecting if complexes between the CD163 and the substance have formed. Substances that bind CD163 in this assay can be further assessed to determine if they are useful in the methods of the invention.

Accordingly, the present invention also includes a method of identifying substances which can bind to CD163 comprising the steps of:

(a) reacting CD163 and a test substance, under conditions which allow for formation of a complex between the CD163 and the test substance, and (b) assaying for complexes of CD163 and the test substance, for free substance or for non complexed CD163, wherein the presence of complexes indicates that the test substance is capable of binding CD163.

Conditions which permit the formation of substance and CD163 complexes may be selected having regard to factors such as the nature and amounts of the substance and the protein.

The substance-CD163 complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against CD163 or the substance, or labelled CD163, or a labelled substance may be utilized. The antibodies, CD163, or substances may be labelled with a detectable substance.

The CD163 or the test substance used in the method of the invention may be insolubilized. For example, the CD163 or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, silica, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized CD163 or substance may be prepared by reacting the material with a suitable insoluble carrier using known chemical or physical methods, for example, cyanogen bromide coupling.

The CD163 or test substance may also be expressed on the surface of a cell in the above assay.

III. Compositions

The present invention also includes pharmaceutical compositions containing the substances that can activate CD163 for use in stimulating hematopoiesis, stimulating erythropoiesis, stimulating myelopoiesis or for stimulating the growth, proliferation, differentiation and/or mobilization of stem cells and/or progenitor cells. Accordingly, the present invention provides a pharmaceutical composition for stimulating hematopoiesis comprising an effective amount of a substance which can activate CD163 in admixture with a suitable diluent or carrier. The present invention also provides a pharmaceutical composition for stimulating erythropoiesis comprising an effective amount of a substance which can activate CD163 in admixture with a suitable diluent or carrier. The present invention also provides a pharmaceutical composition for stimulating myelopoiesis comprising an effective amount of a substance which can activate CD163 in admixture with a suitable diluent or carrier. The present invention further provides a pharmaceutical composition for stimulating stem cell growth, proliferation, differentiation and/or mobilization comprising an effective amount of a substance which can activate CD163 in admixture with a suitable diluent or carrier. The present invention further provides a pharmaceutical composition for stimulating erythroid and/or myeloid cell growth, proliferation, differentiation and/or mobilization comprising an effective amount of a substance which can activate CD163 in admixture with a suitable diluent or carrier.

For stimulating erythropoiesis, the pharmaceutical composition may additionally contain one or more hematopoietic growth factors such as erythropoietin. For stimulating myelopoiesis, the pharmaceutical composition may additionally include one or more hematopoietic growth factors such as G-CSF, GM-CSF, IL-3, etc.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as other agents that can stimulate hematopoiesis, erythropoiesis or myelopoiesis, or can stimulate the growth, proliferation, differentiation and/or mobilization of stem cells and/or progenitor cells.

IV. Culture Additives

The substances that activate CD163 can be used as additives to culture medium for enhancing the growth, proliferation, differentiation and/or mobilization of mammalian progenitor or stem cells or for stimulating hematopoiesis, erythropoiesis or myelopoiesis. Accordingly, the present invention provides a cell culture additive useful for enhancing growth, proliferation, differentiation and/or mobilization of progenitor and/or stem cells comprising an effective amount of a substance that can activate CD163. Substances that activate CD163 can be added to a serum-free medium traditionally used for the expression of hematopoietic stem cells. For example, a serum-free medium with the addition of growth factors such as stem cell factor (SCF), interleukin 3 (IL-3), GM-CSF, Flt ligand (FL), thrombopoietin (TPO) and granulocyte-colony stimulating factor (G-CSF) (as described by Kobari et al., 2000) can be supplemented with a substance that can activate CD163.

V. Cell Enrichment or Detection

As hereinbefore mentioned, the inventors have demonstrated the presence of the CD163 receptor on $CD34^+$ cells derived from umbilical cord blood or adult bone marrow or peripheral blood. The presence of CD163 on these cells may provide an important research and clinical tool as the $CD34^+$/$CD163^+$ sub-population of cells can be further examined for their ability to re-engraft and repopulate the various compartments of the hematopoietic system. In addition, "stem" cells derived from a variety of sources (bone marrow, mobilized peripheral blood or umbilical cord blood) may be enriched for, or sorted by, the expression of CD163.

Accordingly, the present invention provides a method of selecting hematopoietic progenitor or stem cells in a sample comprising (a) contacting the sample with a substance that can bind CD163 and (b) selecting cells that are bound to the substance.

In a preferred embodiment, the substance is an antibody that can bind CD163 and the cells are selected using immunochemical techniques. For example stem cells expressing the CD163 receptor may be "sorted" or selected by employing an anti-CD163 antibody, by complexing this antibody to a solid support, removing the CD163 positive cells from the other cells in the sample and subsequently removing the CD163 positive cells from the solid support. For example, anti-CD163 antibodies can be complexed to magnetic beads. CD163 positive cells can be bound to the antibody and CD163 positive cells can be removed from other cells in the sample with a magnetic source. Upon separation from the non-CD163 positive cells, the CD163 positive cells can be detached from the magnetic beads. Alternatively, the expression of CD163 cells on stem cells may by used to sort these cells through fluorescence-activating cell sorting (FACS) by employing an anti-CD163 fluorescently-labelled Many other methods to purify the CD163 positive cells would be obvious to one skilled in the art. The method can be used to select cells capable of forming colonies of both the erythroid and myeloid lineages or cells that are potentially capable of repopulating organisms with cells of both the erythroid and myeloid lineages. Accordingly, the present invention provides a method to select cells capable of forming colonies of both the erythroid and myeloid lineages comprising (a) contacting the sample with a substance that can bind CD163 and (b) selecting cells that are bound to the substance, wherein the bound cells are capable of forming colonies of both the erythroid and myeloid lineages. The present invention also provides a method to select cells that are potentially capable of repopulating organisms with cells of both erythroid and myeloid lineages comprising (a) contacting the sample with a substance that can bind CD163 and (b) selecting cells that are bound to the substance, wherein the bound cells are potentially capable of repopulating organisms with cells of both erythroid and myeloid lineages.

The invention also includes the use of a substance that binds to CD163, such as an antibody, in a negative selection protocol to remove progenitor or stem cells from a sample. Accordingly, the present invention provides a method of removing hematopoietic cells from a sample comprising (a) contacting the sample with a substance that can bind CD163 and (b) removing the cells that bind to the substance from the sample.

The following non-limiting examples are illustrative of the present invention:

EXAMPLES

Example 1

CD163 is Expressed by $CD34^+$ Cells $CD34^+$ cells derived from cryopreserved adult bone marrow (ABM) were permeabilized using Cytofix/Cytoperm solution (Pharmingen Transduction Laboratories, a division of BD BioSciences; Becton, Dickson and Company) for 30 minutes at 4° C., washed and then incubated with either fluorescently labeled isotypic control antibody (IgG1-FITC) or fluorescently labeled Mac-158 mouse anti-human CD163 monoclonal antibody (MBS; Mac158-FITC). In parallel experiments, cells from the same bone marrow samples were also stained extracellularly with fluorescently labeled anti-CD34 (HPCA-2-PE) and anti-CD45 (H130-FITC). Samples were analyzed using an EPICS XL flow cytometer (Beckman Coulter, Inc)(Results presented in Table 1 indicate that over 95% of the bone marrow cells were $CD34^+/CD45^+$ and the majority of these cells also stained with the anti-CD163 antibody.

TABLE 1

Flow Cytometric Analysis of $CD34^+$ Bone Marrow Cells

|  | % $CD45^+/CD34^+$ | % IgG1 isotype control | % $CD163^+$ |
| --- | --- | --- | --- |
| ABM $CD34^+$ cells | 95 | 1.9 | 75.1 |

Example 2

CD163 Expressed by $CD34^+$ Cells is Detectable by Western Blot

Cell lysates were prepared from $CD34^+$ cells derived from adult bone marrow by resuspending the cells in CHAPS buffer (0.5% CHAPS, 10 mM Tris, 1 mM $MgCl_2$, 1 mM EDTA and 10% glycerol) containing a protease inhibitor cocktail. The resuspended cells were incubated on ice for 30 minutes. Lysates were centrifuged and the supernatant was transferred to a fresh tube. For Western blot analysis, the supernatant was resuspended in non-reducing SDS-sample loading buffer. Samples were then electrophoresed through an 8% polyacrylamide gel and transferred to a nylon filter. The nylon filters were blocked in a skim milk containing solution and then probed first with the Mac-158 anti-human CD163 antibody, followed by a goat-anti-mouse antibody conjugated to horse radish peroxidase (BIO-RAD Laboratories, Inc.). Bound secondary antibody was detected using an enhanced chemiluminescence kit from Amersham plc.

As demonstrated in FIG. 1, CD163 immunoreactivity is detectable in the cell lysate prepared from $CD34^+$ cells.

Example 3

Cell Surface Expression of CD163 on $CD34^+$ Cells

The level of extracellular expression of CD163 by $CD34^+$ cells was determined using flow cytometric analysis of cryopreserved $CD34^+$ cells derived from adult bone marrow and umbilical cord blood (UCB) low density mononuclear cells (LDMNC). Cells were stained with fluorescently labeled anti-CD34 (HPCA-2-PE) and anti-CD163 (Mac158-FITC) antibodies and then analyzed using an EPICS XL flow cytometer. Results are presented in Table 2.

TABLE 2

Co-expression of CD163 and CD34

| Preparation | % $CD163^+$ | % $CD34^+$ | % $CD34^+/CD163^+$ |
| --- | --- | --- | --- |
| $CD34^+$-enriched cells from ABM (n = 4) | 1.6 | 87.9 | 1.7 |
| $CD34^+$-enriched cells from UCB (n = 2) | 2.8 | 25.5 | 3.8 | n = number of samples

The majority of $CD163^+$ cells co-stained with the anti-CD34 antibody, indicating CD163 is expressed by $CD34^+$ cells. The human CD163 receptor has previously been described as a receptor expressed exclusively on monocyte/macrophage-like cells. These data demonstrate that CD163 is also expressed by a population of human hematopoietic stem cells.

Example 4

Stimulation of CD163 Receptors Results in the Growth of Erythroid Cells

The effect of a mouse anti-human anti-CD163 monoclonal antibody (EDHu-1, Serotec) was tested in a colony-forming assay under conditions which support erythroid progenitor colonies (BFU-E). These colonies are formed by single primitive erythroid progenitor cells in semi-solid medium and are relatively large and multi-clustered. Cells within the colony are typically hemoglobinized after 12 to 16 days in culture. $CD34^+$ cells, enriched from umbilical cord blood (UCB), or $CD34^+$ cells derived from adult bone marrow (ABM) were seeded into methylcellulose with 10 ng/mL interleukin-3 (IL-3) and 2 U/mL erythropoietin (Epo), in the absence or presence of 50 ug/mL anti-CD163 antibody. The effect of the antibody on erythroid progenitor number was assessed and the results are demonstrated in Table 3:

TABLE 3

$CD34^+$ cells from ABM or UCB Stimulated in CFA by anti-CD163 antibodies (Ab)

| | No. of BFU-E/1 × $10^3$ cells | | |
| --- | --- | --- | --- |
| Cell source | −Anti-CD163 Ab | +Anti-CD163 Ab | RFI* |
| UCB $CD34^+$ | 28 | 42 | 1.5× |
| ABM $CD34^+$ | 22 | 29 | 1.3× |

*relative fold increase

Anti-CD163 antibody, at 50 ug/ml, resulted in a greater number of BFU-E than those in the corresponding control plates. Similar results were also obtained using a different anti-CD163 antibody (Mac158) to stimulate CD163. The stimulation of $CD34^+$ cells via the CD163 receptor increases the proliferation of erythroid progenitors present in umbilical cord blood or adult bone marrow.

Example 5

Figure 2:
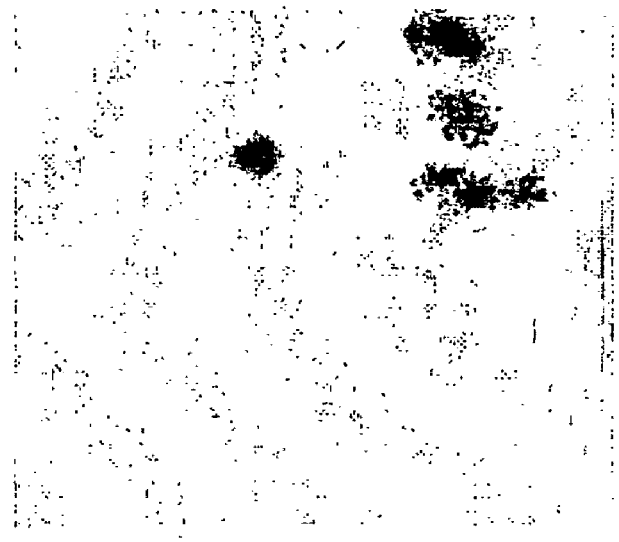
FIG. 2 shows the effect of an antibody to CD163 in hematopoietc colony forming assays.
Figure 2:

Stimulation of CD163 Increases the Proliferation and Differentiation of Erythroid Cells The effect of an activating anti-CD163 antibody was tested in the colony forming assay under conditions that support the formation of erythroid progenitor colonies. $CD34^+$ cells, enriched from umbilical cord blood LDMNC were seeded into methylcellulose (1,000 cells/mL) containing 10 ng/mL IL-3 and 2.0 U/mL Epo, in the presence of either an isotype control antibody (50 ug/mL) or an anti-CD163 antibody (EDHu-1; 50 ug/mL). Methylcellulose plates were incubated in a humidified incubator with 5% $CO_2$, and maintained at 37° C. Colonies (BFU-E) were enumerated and their morphology assessed after 14 days. In addition to increasing the number of erythroid colonies, as demonstrated in Example 4, the anti-CD163 antibody also increased the size and redness of the erythroid progenitor colonies, as compared to the isotype control (FIG. 2). Similar results were also obtained using a different anti-CD163 antibody (Mac158) to stimulate CD163. Similar results were also obtained using CD34+ cells derived from adult bone marrow. These data suggest that stimulation of CD163 increases the proliferation (increased colony size) and the differentiation (increased hemoglobin production and hence redder colonies) of the erythroid cells present in the BFU-E colonies.

Example 6

CD163 is expressed by erythroid cells

Adult bone marrow CD34+ cells were seeded into methylcellulose (1,000 cells/mL) in the presence of 10 ng/mL IL-3 and either 0.5 or 2.0 U/mL Epo. Methylcellulose plates were incubated in a humidified incubator with 5% $CO_2$ and maintained at 37° C. After 14 days, cells from the BFU-E colonies were harvested from the plates, washed, enumerated and pelleted. Cell pellets were frozen at −80° C. Cell lysates were prepared from an equivalent number of cells and an equal volume of lysate per condition was subjected to Western blot analysis as described in Example 3.

Figure 3:
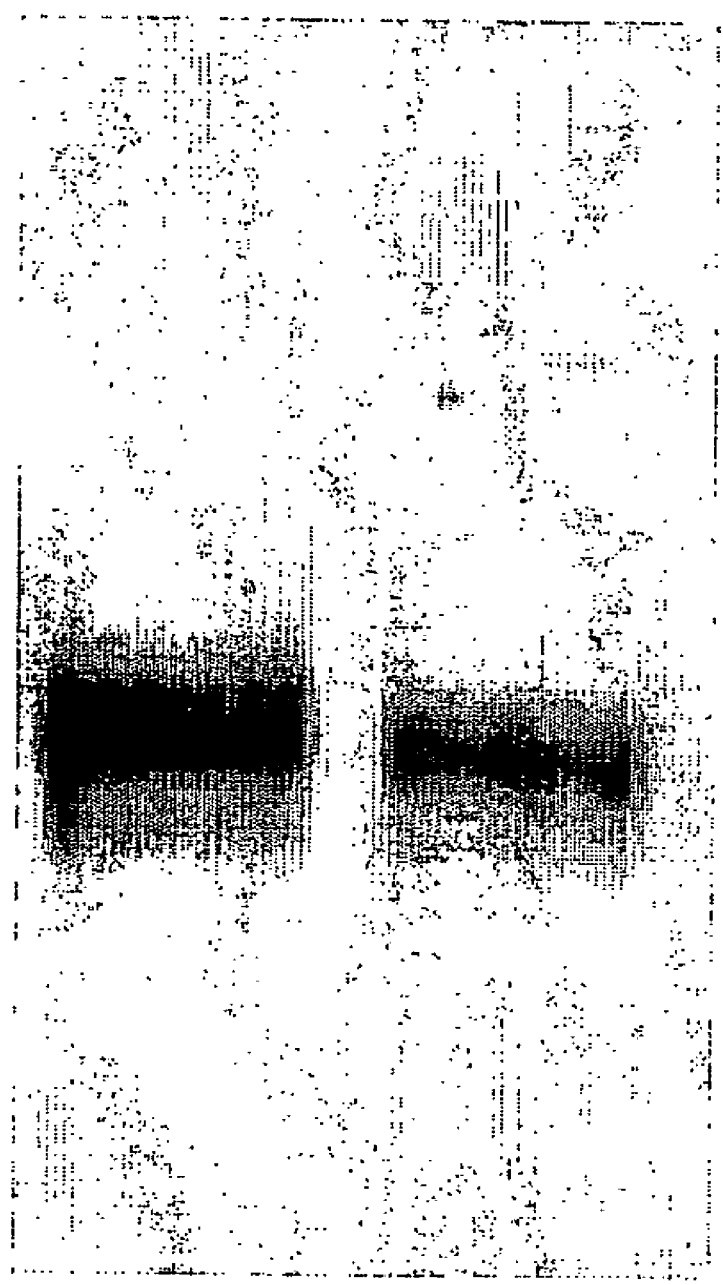
FIG. 3 shows that CD163 immunoreactivity is detectable in the cell lysates prepared from BFU-E colonies.

As shown in FIG. 3, CD163 immunoreactivity is readily detectable in the cell lysates prepared from the BFU-E colonies. Furthermore, under conditions of reduced Epo concentrations, the level of CD163 immunoreactivity is increased, suggesting that Epo may modulate the expression of CD163.

Example 7

CD163 Stimulation Compensates for Sub-Optimal EPO Concentrations

The effect of CD163 antibodies was also tested in serum-free colony forming assays. Adult peripheral blood low density mononuclear cells (APB LDMNC) were seeded ($1 \times 10^5$ cells/mL) into methylcellulose containing 1% BSA, 10 ug/mL insulin, 200 ug/mL human transferrin, 10 ng/mL IL-3 and either 0.2 or 2.0 U/mL EPO, with or without two different anti-CD163 antibodies, EDHu-1 or Mac158. Plates were incubated for 14 days at 37° C. at 5% $CO_2$, after which erythroid progenitor colonies were enumerated. As demonstrated in Table 4, more BFU-E colonies were detected when cells were treated with anti-CD163 antibodies as compared to the untreated cells. Furthermore, the colonies which formed in the presence of the anti-CD163 antibody were bigger and redder than those that formed in the absence of the anti-CD163 antibody. Thus CD163 activation results in an increased proliferation of erythroid progenitors, and an increase in the proliferation and differentiation of erythroid cells within the BFU-E colonies under serum-containing and serum-free colony forming assays. Under conditions of reduced EPO, stimulation of CD163 with either EDHu-1 or Mac158 resulted in an increase in the number of erythroid progenitor colonies (Table 4). These colonies were also bigger and redder than those present in the control plates. Similar results were obtained using CD34+ isolated from adult bone marrow or umbilical cord blood. Similar results were also obtained in serum-containing colony forming assays. In the absence of Epo, no erythroid colonies were detected in the colony forming assays, either in the presence or absence of anti-CD163 antibodies.

These data suggest that the stimulation of CD163 increases the proliferation of erythroid progenitors, as well as, the proliferation and differentiation of the erythroid cells with decreasing EPO concentrations in both serum-containing and serum-free assays. However, stimulation of CD163 cannot replace EPO entirely in the formation of erythroid colonies.

TABLE 4

Stimulation of BFU-E in the Absence or Presence of Anti-CD163 Antibodies (Ab) at High and Low Concentrations of EPO in Serum - Free CFA

| | | Number of BFU-E colonies/plate | | |
|---|---|---|---|---|
| Antibody | [Epo], U/mL | −Anti-CD163 Ab | +Anti-CD163 Ab | RFI* |
| EDHu-1 | 0.2 | 29 | 38 | 1.3 |
| | 2.0 | 48 | 72 | 1.5 |
| Mac158 | 0.2 | 33 | 41 | 1.3 |
| | 2.0 | 48 | 74 | 1.5 |

*relative fold increase

Example 8

Stimulation of CD163 Increases the Proliferation of CFU-GM Progenitors

The effect of the cross-linking anti-CD163 antibody (EDHu-1) was tested in colony forming assays under conditions optimized for the growth of myeloid progenitor (CFU-GM) colonies (50 ng/ml SCF, 4 pg/ml IL-1β, 6.25 ng/ml IL-6). CD34+ derived from umbilical cord blood were seeded in methylcellulose at a concentration of $2 \times 10^3$ cells/ml, with or without 50 ug/ml anti-CD163 antibodies. The effect of the anti-CD163 antibody on the number of CFU-GM was assessed after 14 days of culture at 37° C. and is present in Table 5.

TABLE 5

The anti-CD163 antibody stimulates CFU-GM proliferation

| | CFU-GM per $2 \times 10^3$ cells |
|---|---|
| Control | 130 |
| +50 ug/ml EDHu-1 | 219 |

At 50 ug/ml, the EDHu-1 antibody resulted in a 1.7 fold increase in the number of CFU-GM when compared to the control sample. This suggests that early myeloid progenitors express the CD163 receptor and that stimulation of this receptor increases the proliferation of these cells.

Example 9

CD163 is Expressed by Myeloid Cells Within the CFU-GM Colony and Its Expression is not Limited to CD14+ Cells CD34+ derived from umbilical cord blood cells were seeded into methylcellulose at a concentration of $2 \times 10^3$ cells/ml under conditions optimized for the growth of myeloid progenitor (CFU-GM) colonies (50 ng/ml SCF, 4 pg/ml IL-1b, 6.25 ng/ml IL-6) and cultured in a humidified incubator at 37° C. with 5% $CO_2$. After 14 days, cells from the resultant colonies were harvested, washed, enumerated and examined by flow cytometry for the expression of CD14 and CD163 using the TUK4 and Mac158 fluorescently labeled antibodies, respectively. Results are presented in Table 6.

TABLE 6

Expression of CD163 and CD14 on Cells from CFU-GM colonies

| | CD163+ cells | CD14+ cells | CD163+/CD14+ |
|---|---|---|---|
| CFU-GM derived cells | 10.6% | 42.0% | 1.4% |

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A method of stimulating the growth, proliferation, and/or differentiation of a stem cell that expresses CD163 comprising administering an effective amount of an antibody or fragment thereof that can activate CD163 on the stem cell to the cell or an animal in need thereof.

2. The method according to claim 1 wherein the stem cell is a CD34 positive cell.

3. The method according to claim 1 for the stimulation of hematopoiesis.

4. The method according to claim 1 wherein the stem cell is an erythroid progenitor cell.

5. The method according to claim 1 wherein the stem cell is a myeloid progenitor cell.

6. The method according to claim 1 wherein the antibody or fragment thereof binds to the CD163 on the stem cell.

* * * * *